United States Patent [19]

Schleppnik

[11] 4,128,509
[45] Dec. 5, 1978

[54] 1-(NORBORN-5'-EN-2'-YL) OR 1-(NORBORN-2'-YL) SUBSTITUTED 1-ALKEN-3-OLS AND ALKAN-3-OLS

[75] Inventor: Alfred A. Schleppnik, St. Louis, Mo.

[73] Assignee: Monsanto Company, St. Louis, Mo.

[21] Appl. No.: 528,124

[22] Filed: Nov. 29, 1974

Related U.S. Application Data

[63] Continuation-in-part of Ser. No. 211,788, Dec. 23, 1971, abandoned.

[51] Int. Cl.$^2$ .................. C07C 35/22; A61K 7/46
[52] U.S. Cl. .................. 252/522; 252/89 R; 252/108; 568/820
[58] Field of Search .................. 260/617 F; 252/522

[56] References Cited

U.S. PATENT DOCUMENTS

| | | | |
|---|---|---|---|
| 3,662,088 | 5/1972 | Kretschman et al. | 260/617 F |
| 3,673,256 | 6/1972 | Pieper et al. | 260/617 F |
| 3,673,261 | 6/1972 | Kretschman et al. | 260/617 F |
| 3,679,756 | 7/1972 | Kretschman et al. | 260/617 F |

OTHER PUBLICATIONS

Beilstein, 3rd Erg., System, #509, pp. 341-342, sixth band.
Nazaror et al., Chem. Abst., vol. 42, Col. 7728, (1948).

*Primary Examiner*—James O. Thomas, Jr.
*Assistant Examiner*—James H. Reamer
*Attorney, Agent, or Firm*—R. E. Wexler; H. C. Stanley; E. P. Grattan

[57] ABSTRACT 1-(Norborn-5'-en-2'-yl) or 1-(norborn-2'-yl) substituted 1-alken-3-ols and alkan-3-ols characterized by the structural formulae

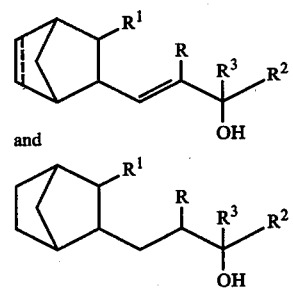

and wherein $R^1$ represents hydrogen or methyl, R represents an alkyl with from 1 to 8 carbon atoms, and $R^2$ and $R^3$ represent hydrogen or an alkyl with from 1 to 8 carbon atoms, provided that R and $R^2$ can be —$CH_2$—$_n$ wherein n represents the integer 2, 3 or 4. The compounds have very pleasant, lasting floral-woody aromas and are useful as components in fragrance compositions.

18 Claims, No Drawings

1-(NORBORN-5'-EN-2'-YL) OR 1-(NORBORN-2'-YL) SUBSTITUTED 1-ALKEN-3-OLS AND ALKAN-3-OLS

This application is a continuation-in-part of our co-pending application, Ser. No. 211,788, filed Dec. 23, 1971.

This invention relates to the art of fragrance compositions and, more particularly, to a novel class of compounds possessing a characteristic aroma. More specifically, this invention is directed to a novel class of useful compounds, their preparation and the utility of these compounds as fragrances.

The art of perfumery began, perhaps, in the ancient cave dwellings of prehistoric man. From its inception, and until comparatively recently, the perfumer has utilized natural perfume chemicals of animal and vegetable origin. Thus, natural perfume chemicals such as the essential oils, for example, oil of rose and oil of cloves, and animal secretions such as musk, have been manipulated by the perfumer to achieve a variety of fragrances. In more recent years, however, research perfume chemists have developed a large number of synthetic odoriferous chemicals possessing aroma characteristics particularly desired in the art. These synthetic aroma chemicals have added a new dimension to the ancient art of the perfumer, since the compounds prepared are usually of a stable chemical nature, are inexpensive as compared with the natural perfume chemicals and lend themselves more easily to manipulation than natural perfume chemicals since such natural perfume chemicals are usually a complex mixture of substances which defy chemical analysis. In contrast thereto, the synthetic aroma chemicals possess a known chemical structure and may therefore be manipulated by the perfumer to suit specific needs. Accordingly, there is a great need in the art of fragrance compositions for new compounds possessing specific characteristic aromas.

The principal object of the present invention is to provide a new class of aroma chemicals consisting of 1-(norborn-5'-en-2'-yl) or 1-(norbon-2'-yl) substituted 1-alken-3-ols and alkan-3-ols.

Another object of the present invention is to provide a specific class of norbornenyl and norbornyl-alkenols and alkanols having a characteristic aroma which can be utilized in the preparation of fragrances and fragrance compositions.

These and other objects, aspects and advantages of this invention will become apparent from a consideration of the accompanying specification and claims.

In accordance with the above objects, there is provided by the present invention a novel class of compounds characterized by the structural formulae

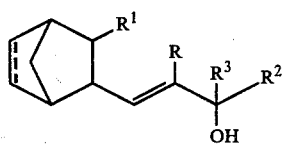

I and

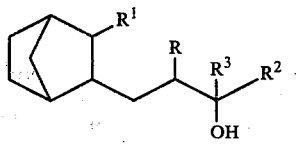

II wherein $R^1$ represents hydrogen or methyl, R represents an alkyl with from 1 to 8 carbon atoms, and $R^2$ and $R^3$ represent hydrogen or an alkyl with from 1 to 8 carbon atoms, provided that R and $R^2$ can be $-(CH_2)_n-$ wherein n represents the integer 2, 3 or 4.

The class of compounds as a whole exhibits a characteristic pleasant, lasting floral-woody aroma, which is useful in the preparation of fragrance compositions and perfumed products.

Representative alkyl groups characterized by R, $R^2$ and $R^3$ in the above formulae include methyl, ethyl, n-propyl, i-propyl, n-butyl, i-butyl, tert-butyl, n-amyl, i-amyl, tert-amyl, n-octyl and the like.

Representative combinations of R and $R^2$ are ethylene, propylene and butylene.

The compounds characterized by structural formula I, wherein $R^3$ is alkyl, can be prepared by reacting a compound characterized by the structural formula

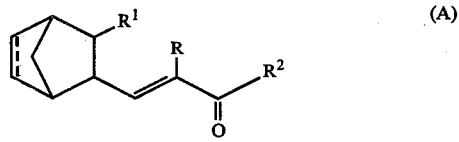

(A)

wherein R, $R^1$ and $R^2$ have the same meaning as defined hereinabove, with a Grignard reagent or lithium alkyl reagent characterized by the formulae, $R^3MgX$ or $R^3Li$, respectively, wherein $R^3$ is lower alkyl of from 1 to 8 carbon atoms and X is a halogen. Such reactions are illustrated by the following equation:

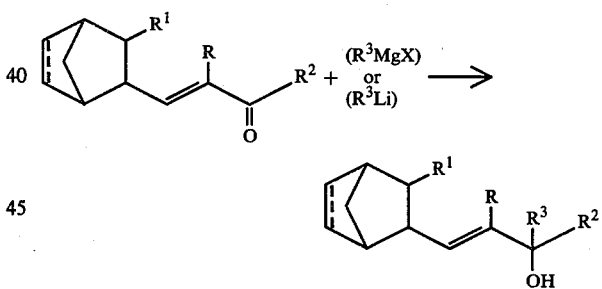

The compounds characterized by structural formula I, wherein $R^3$ is hydrogen, can be prepared by reduction of the compounds characterized by the structural formula (A), above, with mixed metal hydrides, for instance, lithium aluminum hydride, sodium borohydride or sodium tris-methoxy ethoxy aluminum hydride, or by hydrogenation over suitably activated palladium or iridium catalysts under controlled conditions of temperature and pressure. Such a reaction is illustrated by the following equation (wherein the illustrative mixed metal hydride, $Na[BH_4]$, is shown):

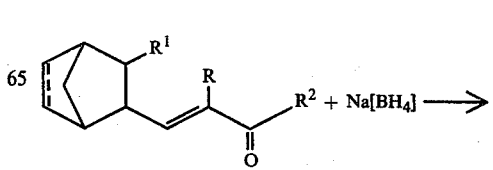

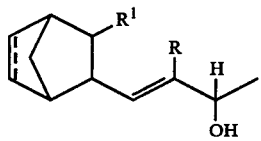
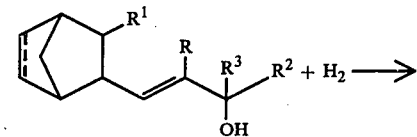

The compounds characterized by the structural formula (A) above can be prepared by processes described in my copending applications Ser. Nos. 103,878 and 103,879 filed Jan. 4, 1971, and identified by case docket Nos. as CO2-21-2614A and CO2-21-2615A respectively. Such processes comprise reacting a norbornane or 5-norbornene carboxaldehyde characterized by the structural formula

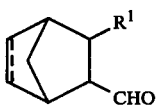

with an aliphatic aldehyde or aliphatic or alicyclic ketone characterized by the structural formula

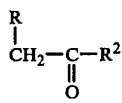

in a basic medium to form an aldol by condensation. Such a reaction is illustrated by the following equation:

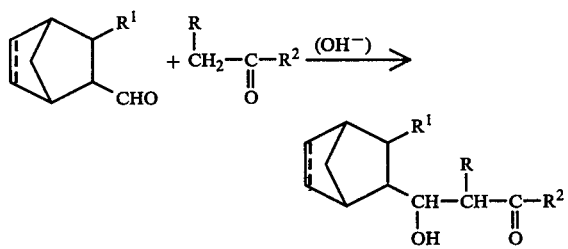

wherein $R^1$, R and $R^2$ have the same meaning as defined hereinabove.

The resulting aldol can then be dehydrated as illustrated in the following equation to form the compounds characterized by structural formula (A):

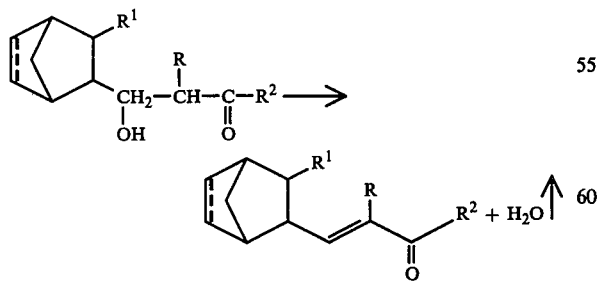

Compounds characterized by the structural formula II can be prepared by hydrogenation of the compounds characterized by the structural formula I as illustrated in the following equation:

This method is useful in, for instance, the preparation of 1-(norborn-2'-yl)-2-methyl-propan-3-ol by the hydrogenation of 1-(norborn-5'-en-2'-yl)-2-methyl-prop-1-en-3-ol or 1-(norborn-2'-yl)-2-methyl-prop-1-en-3-ol over a suitable catalyst.

Alternatively, the compounds characterized by the structural formula II, wherein $R^3$ is alkyl, can be prepared directly from the norbornyl alkanone ($R^2$ is alkyl) or alkanal ($R^2$ is hydrogen) compounds which, in turn can be prepared, as described in my hereinabove noted copending applications from the compounds characterized by the structural formula (A). Reaction of these compounds with a Grignard reagent, $R^3MgX$, as hereinbefore defined, is illustrated in the following equation:

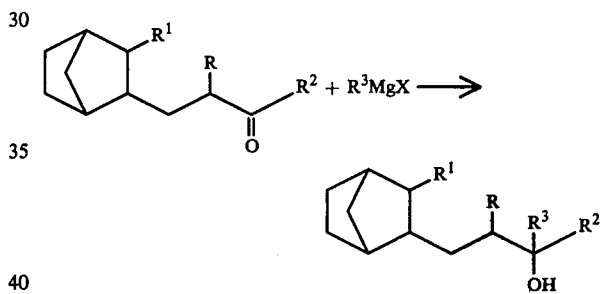

The above illustrated reaction can be utilized to prepare, for instance, 1-(norborn-2'-yl)-2,3-dimethyl-butan-3-ol by the reaction of 1-(norborn-2'-yl)-2-methyl-butan-3-one with methyl magnesium chloride.

The compounds characterized by structural formula II, wherein $R^3$ is hydrogen, can be obtained by reducing the above described norbornyl alkanone or alkanal compounds with mixed metal hydrides or by hydrogenation over platinum or Raney nickel catalysts. Such a reaction is illustrated in the following equation:

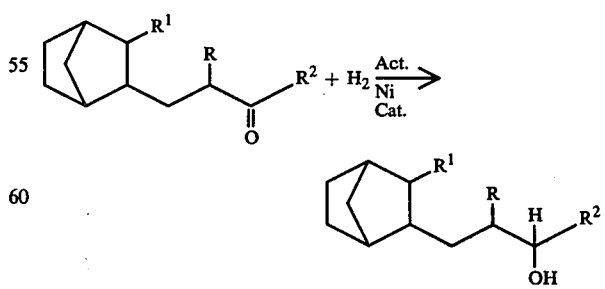

The above illustrated reaction can be utilized to prepared, for instance, 1-(norborn-2'-yl)-2-methyl-propan-3-ol, by the hydrogenation of 1-(norborn-2'-yl)-2-methyl-propan-3-al over a suitable catalyst.

The conditions for the above described reduction and Grignard reactions are not critical but should be such as to facilitate the preparation of the products. Normally, the use of the Grignard reagent in slight excess is preferred. The reactions are normally conducted at temperatures of from about 0° C. to about 50° C.

The substituent groups on the claimed norbornene (ane) nuclei may be spatially related in what is known as "exo" or "endo" positions in three-dimensional representation. It is to be understood, however, that the novel compounds, as generically described and claimed, are intended to embrace both of these configurations. The specific illustrations given are not to be considered as limitations upon the scope of the invention or as restrictive exemplifications of "exo" or "endo" configurations of a given compound.

The novel compounds of this invention are useful in the preparation and formulation of fragrance compositions such as perfumed and perfumed products due to their pleasing and long lasting aromas. Perfume compositions and the use thereof in cosmetic, detergent and bar soap formulations and the like are exemplary of the utility thereof.

The compounds of this invention are used in concentrations of from trace amounts up to about 50 percent of the perfume composition into which they are incorporated. As will be expected, the concentration will vary depending on the particular fragrance composition and even within the same composition when compounded by different perfumers.

The following examples will serve to illustrate certain specific embodiments within the scope of this invention and are not to be construed as limiting the scope thereof.

EXAMPLE 1

1-(norborn-2'-yl)-2-methyl-butan-3-ol

To a solution of 8.9 g. (0.05 mol.) of 1-(norborn-2'-yl)-2-methyl-butan-3-one in 50 ml. methanol was added, with stirring, a solution of 1 g. sodium borohydride in 10 ml. 5% aqueous sodium hydroxide solution. An exothermic reaction took place, the temperature rose to 50° C. (cooling with cold water bath was necessary). The reaction mixture was left at room temperature for fifteen hours and yielded 7.1 g. (80% product), b.p. 115°–118° C./10 mm. having a $n_D^{25} = 1.4820$. The reaction product was found to be 1-(norborn-2'-yl)-2-methyl-butan-3-ol. It was a viscous colorless liquid with a distinct woody aroma.

EXAMPLE 2

1-(norborn-5'-en-2'-yl)-2,3-dimethyl-but-1-en-3-ol

The title compound can be prepared by adding a solution of 1-(norborn-5'-en-2'-yl)-2-methyl-but-1-en-3-one in ether, with stirring and cooling, to one equivalent of methyl lithium in ether maintaining the solution formed at room temperature for 15 hours.

EXAMPLE 3

1-(norborn-2'-yl)-2-methylprop-1-en-3-ol

The title compound can be prepared by adding a solution of sodium borohydride in aqueous ethanol to a solution of 1-(norborn-2'-yl)-2-methylprop-1-en-3-al in ethanol.

EXAMPLE 4

1-(norborn-5'-en-2'-yl)-2-methylpent-1-en-3-ol

The title compound can be obtained by reacting ethyl magnesium bromide with 1-(norborn-5'-en-2'-yl)-2-methylprop-1-en-3-al.

EXAMPLE 5

1-(norborn-2'-yl)-2-methylpentan-3-ol

The title compound can be obtained by the hydrogenation of 1-(norborn-5'-en-2'-yl)-2-methylpent-1-en-3-one over Raney nickel and ethanol solution at 100 psi. H₂ pressure and 80° C.

EXAMPLE 6

1-methyl-2-(norborn-2'-yl-methyl) cyclopentan-1-ol

The title compound is obtained by reacting 2-(norborn-2'-yl-methyl) cyclopentenone and methyl magnesium bromide in ether.

While the invention has been described herein with regard to certain specific embodiments, it is not so limited. It is to be understood that variations and modifications thereof may be made by those skilled in the art without departing from the spirit and scope of the invention.

The embodiments of this invention in which an exclusive property or privilege is claimed are defined as follows:

1. A compound characterized by the formulae

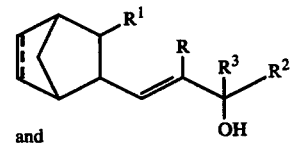

and

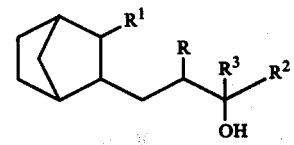

wherein $R^1$ represents hydrogen or methyl, R represents an alkyl with from 1 to 8 carbon atoms, and $R^2$ and $R^3$ represent hydrogen or an alkyl with from 1 to 8 carbon atoms, provided that R and $R^2$ can be $-(CH_2)_n-$ wherein n represents the integer 2, 3 or 4.

2. A compound as defined in claim 1 wherein $R^1$ is hydrogen.

3. A compound as defined in claim 1 wherein $R^3$ is hydrogen.

4. A compound as defined in claim 1 wherein $R^1$ and $R^3$ are hydrogen.

5. A compound as defined in claim 1 which is characterized by the structural formula:

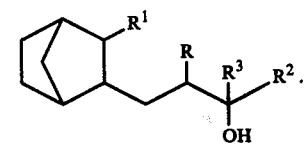

6. A compound as defined in claim 5 wherein $R^1$ is hydrogen.

7. A compound as defined in claim 6 which is 1-(norborn-2'-yl)-2,3-dimethyl-butan-3-ol.

8. A compound as defined in claim 6 wherein $R^3$ is hydrogen.

9. A compound as defined in claim 8 which is 1-(norborn-2'-yl)-2-methyl-propan-3-ol.

10. A compound as defined in claim 8 which is 1-(norborn-2'-yl)-2-methyl-butan-3-ol.

11. In the method of preparing a fragrance composition, the step comprising incorporating therein an odoriferous amount of a compound as defined in claim 1.

12. The method of claim 11 wherein the compound incorporated is characterized by the structural formula

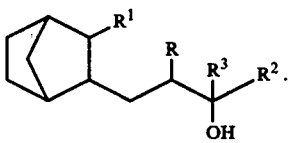

13. The method of claim 12 wherein $R^1$ is hydrogen.

14. The method of claim 13 wherein $R^3$ is hydrogen.

15. A fragrance composition having incorporated therein an odoriferous amount of a compound as defined in claim 1.

16. A fragrance composition of claim 15 wherein the compound incorporated therein is characterized by the structural formula

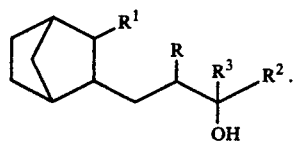

17. A fragrance composition of claim 16 wherein $R^1$ is hydrogen.

18. A fragrance composition of claim 16 wherein the compound incorporated therein is 1-(norborn-2'-yl)-2-methyl-butan-3-ol.

* * * * *